(12) United States Patent
Pesonen et al.

(10) Patent No.: US 11,421,197 B2
(45) Date of Patent: Aug. 23, 2022

(54) APPARATUS FOR CONTROLLING FERMENTATION OF NATURAL MATERIAL

(71) Applicant: QUANTURI OY, Espoo (FI)

(72) Inventors: Nadine Pesonen, Siuntio (FI); Roland Guerre, Espoo (FI)

(73) Assignee: QUANTURI OY, Espoo (FI)

( * ) Notice: Subject to any disclaimer, the term of this patent is extended or adjusted under 35 U.S.C. 154(b) by 739 days.

(21) Appl. No.: 16/071,278

(22) PCT Filed: Jan. 20, 2017

(86) PCT No.: PCT/FI2017/050031
§ 371 (c)(1),
(2) Date: Jul. 19, 2018

(87) PCT Pub. No.: WO2017/125648
PCT Pub. Date: Jul. 27, 2017

(65) Prior Publication Data
US 2021/0198614 A1      Jul. 1, 2021

(30) Foreign Application Priority Data

Jan. 22, 2016  (FI) ...................................... 20165041

(51) Int. Cl.
*C12M 1/36* (2006.01)
*A01F 25/00* (2006.01)
*A01F 15/08* (2006.01)

(52) U.S. Cl.
CPC ............. *C12M 41/48* (2013.01); *A01F 25/00* (2013.01); *C12M 1/36* (2013.01); *A01F 15/08* (2013.01)

(58) Field of Classification Search
CPC .......... C12M 41/48; C12M 1/36; A01F 25/00; A01F 15/08; A01F 15/0816
See application file for complete search history.

(56) References Cited

U.S. PATENT DOCUMENTS 4,184,159 A * 1/1980 Andersson ................ G01S 3/02
                                                          340/870.11
4,913,914 A    4/1990 Hashimoto et al.
(Continued)

FOREIGN PATENT DOCUMENTS

AU   2011211394 A1   3/2012
CN    201060201 Y    5/2008
(Continued)

OTHER PUBLICATIONS

Office Action dated Jun. 13, 2019, by the Canadian Patent Office in corresponding Canadian Patent Application No. 3,011,909. (5 pages).
(Continued)

*Primary Examiner* — Michael L Hobbs
(74) *Attorney, Agent, or Firm* — Buchanan Ingersoll & Rooney PC

(57) ABSTRACT

An apparatus for controlling fermentation of natural material. The apparatus includes one or more sensors configured to measure at least one property of natural material, a container configured to contain a chemical reactive agent reducing or limiting a fermentation process of the natural material; a valve coupled with the container; and a controller configured to process the measured at least one property of the natural material, and, if the processing meets a predetermined condition, control the valve to open so that the chemical reactive agent is released into the natural material in order to limit the fermentation process of the natural material.

6 Claims, 2 Drawing Sheets

(56) References Cited

U.S. PATENT DOCUMENTS

| | | | |
|---|---|---|---|
| 5,377,551 A | 1/1995 | Vacquer | |
| 5,744,189 A | 4/1998 | Pieper | |
| 6,502,505 B1 | 1/2003 | Yun | |
| 8,633,820 B2 | 1/2014 | Jonsson et al. | |
| 2002/0117445 A1 | 8/2002 | Whiteman | |
| 2002/0152037 A1 | 10/2002 | Sunshine et al. | |
| 2003/0006312 A1* | 1/2003 | Dohrmann | A01F 15/0816 239/329 |
| 2005/0118703 A1* | 6/2005 | Su | C12M 41/48 435/286.1 |
| 2008/0064022 A1 | 3/2008 | Murthy et al. | |
| 2010/0148959 A1* | 6/2010 | Jonsson | H04L 67/12 340/540 |
| 2012/0125840 A1 | 5/2012 | Smith | |
| 2013/0115588 A1 | 5/2013 | Davis et al. | |
| 2013/0189763 A1 | 7/2013 | Dalla-Betta et al. | |
| 2014/0165854 A1 | 6/2014 | Green et al. | |
| 2015/0177114 A1* | 6/2015 | Kapoor | G01N 33/0098 702/128 |
| 2020/0169854 A1 | 5/2020 | Pesonen et al. | |

FOREIGN PATENT DOCUMENTS

| | | |
|---|---|---|
| CN | 108925130 A | 11/2018 |
| DE | 32 25 577 A1 | 3/1983 |
| DE | 4305638 C1 | 9/1994 |
| EP | 0156176 A1 | 10/1985 |
| GB | 1508293 A | 4/1978 |
| NL | 7508055 A | 1/1977 |
| RU | 2555794 C1 | 7/2015 |

OTHER PUBLICATIONS

Search Report dated May 21, 2019, by the Russian Patent Office in corresponding Russian Application No. 2018127554. (2 pages).

Finnish Search Report of Finnish Patent Application No. 20165041, dated Aug. 26, 2016.

International Search Report (PCT/ISA/210) dated Apr. 4, 2017, by the European Patent Office as the International Searching Authority for International Application No. PCT/FI2017/050031.

Written Opinion (PCT/ISA/237) dated Apr. 4, 2017, by the European Patent Office as the International Searching Authority for International Application No. PCT/FI2017/050031.

First Office Action dated Aug. 13, 2021, by the Chinese Patent Office in corresponding Chinese Patent Application No. 201780013154.6, and an English Translation of the Office Action. (35 pages).

Office Action dated Mar. 2, 2022, by the Chinese Patent Office in corresponding Chinese Patent Application No. 201780013154.6. (4 pages).

* cited by examiner

APPARATUS FOR CONTROLLING FERMENTATION OF NATURAL MATERIAL

FIELD

The invention relates to an apparatus for controlling fermentation of natural material.

BACKGROUND

More than 20 natural products (such as hay, straw, cereals, cottons, fish-based oil and peat) are prone to spontaneous combustion, or auto-combustion, the result of a chemical process that occurs when a damp material heats up and ignites.

The most common method for preventing spontaneous combustion is to remove moisture from the material by letting it naturally dry up. However this is often challenging as the drying process depends strongly on weather conditions if the material is left outside. Some materials such as hay or straw require several days for reaching a complete dryness, a timespan often disrupted by rainy conditions.

Another prevention method is the use of electric dryers to remove moisture by circulating heated air to evaporate the moisture. However this electric solution is not applicable for all products (peat, for example) and is costly as it requires installing a dedicated infrastructure for the process.

Fermentation, which causes spontaneous combustion, can be reduced or even stopped with chemical agents. These solutions are global solutions as they are spread over the whole material independently on the moisture distribution of the material.

Only manual probes to read out temperature and humidity exist. These probes do not provide any continuous monitoring over time nor provide any positive action on the fermentation process.

Consequently, there is a need for a more refined solution for controlling fermentation of natural material.

BRIEF DESCRIPTION

The present invention seeks to provide an improved apparatus for controlling fermentation of natural material.

According to an aspect of the present invention, there is provided an apparatus as specified in claim 1.

The present invention actively controls a fermentation process of natural material, whereby at least one of the following advantages may be provided: desired properties and quality of the natural material may be maintained, and/or a spontaneous combustion of the natural material may be inhibited.

BRIEF DESCRIPTION OF THE DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
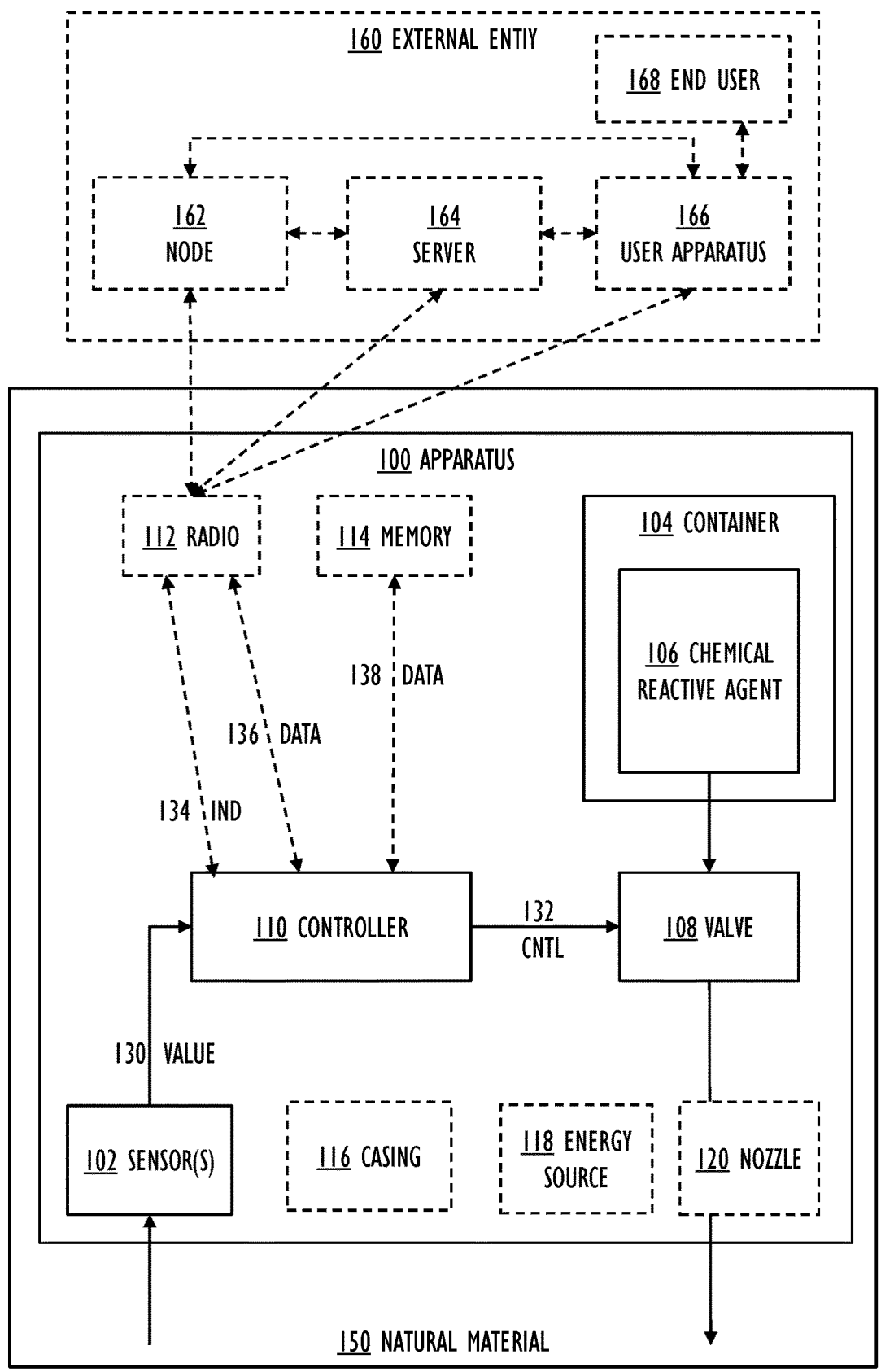
FIGS. 1 and 2 illustrate example embodiments of an apparatus.
Figure 2:
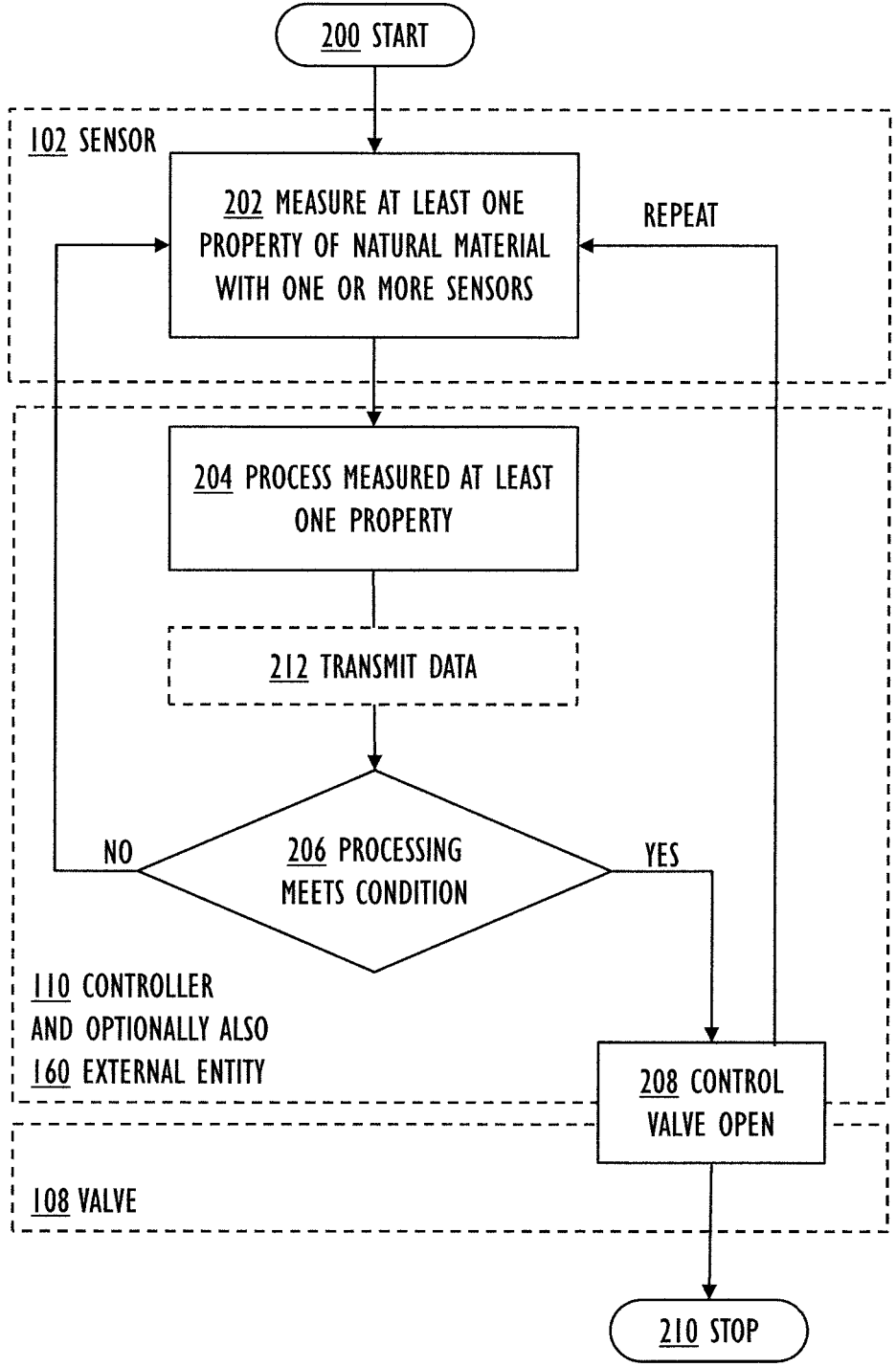

FIG. 1 illustrates an apparatus 100 for controlling fermentation of natural material, and FIG. 2 illustrates the operation of the apparatus 100: the operation starts in 200 and stops in 210.

The apparatus 100 comprises one or more sensors 102 configured to measure 202 at least one property of natural material 150.

In an example embodiment, the natural material 150 comprises at least one of the following: an agriculture product, hay, straw, cereal, hay bale, cotton, peat.

In an example embodiment, the at least one property comprises at least one of the following: a temperature of the natural material 150, a humidity of the natural material 150, a pH of the natural material 150.

In an example embodiment, the sensor 102 is a transducer detecting one form of energy (temperature, for example), and reporting it in another form (such as voltage of an electrical signal). When the sensor 102 measures 202 the property of the natural material 150, it generates a value 130 representing a quantity of the property.

The apparatus 100 also comprises a container 104 configured to contain a chemical reactive agent 106 reducing or limiting a fermentation process of the natural material 150.

In an example embodiment, the container 104 is a tank for a chemical reactive agent fluid 106.

In an example embodiment, the chemical reactive agent 106 comprises at least one of the following: potassium carbonate, sodium carbonate, propionic acid, formic acid, acetic acid, sodium diacetate, anhydrous ammonia, sulphite, potassium sorbate. Also other chemical reactive agents reducing or limiting the fermentation process of the natural material 150 may be applied.

The apparatus 100 also comprises a valve 108 coupled with the container 104. With the valve 108, the flow of the chemical reactive agent (in the form of fluid, i.e., gas, liquid, fluidized solid, or slurry) is regulated and directed by opening/closing various output passageways of the container 104.

In an example embodiment, the container 104 is pressurized, whereby the opening of the valve 108 causes the chemical reactive agent 106 to flow into the natural material 150 due to the pressure.

In an example embodiment, the container 104 is positioned above the valve 108, whereby the opening of the valve 108 causes the chemical reactive agent 106 to flow into the natural material 150 due to the Earth's gravity.

In an example embodiment, the valve 108 is coupled with a pump, whereby the opening of the valve 108 causes the chemical reactive agent 106 to flow into the natural material 150 due to a pumping action by the pump.

In an example embodiment, the valve 108 is couple with a nozzle 120, with which the direction or characteristics of a fluid flow may be controlled: to increase velocity of the flow, or to atomize the fluid in order to distribute it more evenly, for example.

The apparatus 100 also comprises a controller 110, communicatively coupled with the one or more sensors 102 and operatively coupled with the valve 108, configured to process 204 the measured at least one property 130 of the natural material 150, and, if the processing meets 206 YES a predetermined condition, control 132, 208 the valve 108 to open so that the chemical reactive agent 106 is released into the natural material 150 in order to limit the fermentation process of the natural material 150.

In an example embodiment, upon certain conditions, defined by the nature of the natural material 150 and its behaviour over time, triggering of the valve 108 of the container 104 is actuated. Such predetermined condition may relate to one or more properties measured: to temperature, and/or to humidity, and/or to pH (acidity/basicity), for example.

In this way, the apparatus 100 actively controls the fermentation process of the natural material 150, whereby desired properties and quality of the natural material 150 is maintained, and/or a spontaneous combustion of the natural material 150 is inhibited. The apparatus 100 thus meets a need to monitor changes of the properties of natural products 150 over time in order to obtain data about the development and evolution of a possible fermentation, and control actively this fermentation process in order to prevent any danger of spontaneous combustion. Additionally, controlling the fermentation process of the natural material 150 will ensure maintaining its properties and quality. Indeed, any natural materials 150 that have endured severe fermentation will see their value reduced.

If the processing does not meet 206 NO the predetermined condition, operation 202 is re-entered.

In an example embodiment, the valve 108 may be closed after administering only a part of the stored chemical reactive agent 106, whereupon operation 202 may be re-entered.

The decision on actuating the opening the container 104 may either be made at the apparatus 100 level or at a system level (=apparatus 100 interacting with an external entity 160).

In an example embodiment, the controller 110 is configured so that the processing meets the predetermined condition (204 and 206 YES), if the controller 110 autonomously detects that the at least one property meets a predetermined threshold. "Autonomously" means that the controller 110 independently performs the check in 206.

In an alternative example embodiment, the apparatus 100 further comprises a radio transceiver 112, and the controller 110 is configured so that the processing meets the predetermined condition (204 and 206 YES), if, in response to a transmission 212 of the measured at least one property with the radio transceiver 112 to an external entity 160, an indication 134 that the predetermined condition is met is received with the radio transceiver 112 from the external entity 160.

In an example embodiment, the controller 110 is a simple threshold detector implemented with suitable electronics configured to detect whether the at least one measured property meets the predetermined condition (by meeting a threshold value, for example).

In an alternative example embodiment, the controller 110 is a processor, i.e., a device that is capable of processing data.

A non-exhaustive list of implementation techniques for the processor 110 includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

In an example embodiment, the processor 110 may be implemented as a microprocessor implementing functions of a central processing unit (CPU) on an integrated circuit. The CPU is a logic machine executing a computer program code implementing the functionality 204, 206, 208. The computer program code may be coded as a computer program using a programming language, which may be a high-level programming language, such as C, or Java, or a low-level programming language, such as a machine language, or an assembler. The CPU may comprise a set of registers, an arithmetic logic unit (ALU), and a control unit (CU). The control unit is controlled by a sequence of the computer program code transferred to the CPU from a (working) memory. The control unit may contain a number of microinstructions for basic operations. The implementation of the microinstructions may vary, depending on the CPU design. The microprocessor 110 may also have an operating system (a dedicated operating system of an embedded system, a real-time operating system, or even a general-purpose operating system), which may provide the computer program code with system services.

In an example embodiment, the functionality of the processor 110 may be designed by a suitable hardware description language (such as Verilog or VHDL), and transformed into a gate-level netlist (describing standard cells and the electrical connections between them), and after further phases the chip implementing the processor, memory, and the code of processor 110 may be fabricated with photo masks describing the circuitry.

In an example embodiment, the processor 110 is implemented as a microcontroller, which is an embedded computer on a single integrated circuit containing a processor core, memory, and programmable input/output peripherals (to control the valve 108, for example). In an example embodiment, such microcontroller 110 may also include a built-in radio transceiver 112. In an example embodiment, the apparatus 100 further comprises a radio transmitter 112, and the controller 110 is configured to transmit data 136 to an external entity 160, the data comprising 136 one or more of the following: the measured at least one property, information about operation of the apparatus 100, an alarm relating to an abnormal situation.

In an example embodiment, the radio transmitter/transceiver 112 utilizes low frequencies of the ISM band (e.g. but not limited to 13.56 MHz, 26-28 MHz, 430-435 MHz, 860-930 MHz, 2.45 GHz, or 5.8 GHz) for better radio-frequency penetration inside damp material. An antenna of the radio communication module 112 may be designed for matching the radio communication circuit and for radiation in a possible damp environment. In an example embodiment, the radio transceiver 112 is implemented as a cellular radio transceiver and/or a non-cellular radio transceiver. In an example embodiment, the cellular radio transceiver 112 may be interoperable with various wireless standard/non-standard/proprietary cellular radio networks such as any mobile phone network, which may be coupled with a wired network such as the Internet.

In an example embodiment, the wireless communication network comprises any mobile phone network, regardless of the generation (such as 2G, 3G, 4G, beyond 4G, 5G etc.) such as GSM (Global System for Mobile Communications), GPRS (General Packet Radio Service), EGPRS (Enhanced GPRS), WCDMA (Wideband Code Division Multiple Access), UMTS (Universal Mobile Telephone System), 3GPP (The 3rd Generation Partnership Project), IMT (International Mobile Telecommunication), LTE (Long Term Evolution, LTE-A (LTE-Advanced), Mobile WiMAX, and other radio systems (in their present forms and/or in their evolution forms).

In an example embodiment, the communication network supports the use of subscriber identity module (SIM), which may be an integrated circuit storing subscriber data, which is network-specific information used to authenticate and identify the subscriber on the cellular network. The subscriber identity module may be embedded into a removable SIM card. Consequently, the apparatus 100 may include the SIM card (and a SIM card reader). Alternatively, the apparatus 100 may include a virtual or software SIM card.

In an example embodiment, the wireless communication network comprises a wireless local area network (WLAN), a hotspot, or an access point, all of which may provide Internet access for the apparatus 100 through the use of a router connected to a link to an Internet service provider.

In an example embodiment, the non-cellular radio transceiver 112 may utilize a short-range wireless technology, a Bluetooth standard, a Bluetooth low energy (BLE) standard, a wireless local area network (WLAN) standard, a Wi-Fi (or WiFi) standard, a IEEE (Institute of Electrical and Electronics Engineers) 802.11 standard or its evolution versions (IEEE 802.11ac etc.), for example), a proprietary short-range radio technology.

Cells provide radio coverage over a wide geographic area, thus enabling a situation wherein the physical distance between the apparatus 100 and the external apparatus 160 may be quite small, i.e. the apparatus 100 is located in the same cell with the external entity 160, or quite large, i.e. the apparatus 100 is not located in the same cell with the external entity 160. In practice, the distance between the apparatus 100 and the external entity 160 may vary from meters to thousands of kilometres. However, typical distance may be from tens of meters to kilometres or a few hundred kilometres. Picture the following scenario, for example: the apparatuses 100 are inside hay bales in a barn, and the external entity 160 is in an office of a farmer 168.

In an example embodiment, the apparatus 100 further comprises a memory 114, and the controller 110 is further configured to store data 138 in the memory 114.

The term 'memory' 114 refers to a device that is capable of storing data run-time (=working memory) or permanently (=non-volatile memory). The working memory and the non-volatile memory may be implemented by a random-access memory (RAM), dynamic RAM (DRAM), static RAM (SRAM), a flash memory, a solid state disk (SSD), PROM (programmable read-only memory), a suitable semiconductor, or any other means of implementing an electrical computer memory.

In an example embodiment, the external entity 160 may comprise a single entity or a plurality of communicating entities. In an example embodiment, the external entity 160 comprises an external reader, base station or more generally a network node 162 to communicate the monitored data. The node 162 may transmit the data either directly to an end user apparatus 166 or via a server 164. Alternatively, the external entity 160 may comprise only the server 164 and/or the user apparatus 166. The role of the node 162 and/or the server 164 is to manage a plurality of apparatuses 100 operated on the field.

In an example embodiment, the user apparatus 166 may comprise a communication apparatus of the end user 168. A non-exhaustive list of the types of the communication apparatus 166 includes: a smartwatch, a mobile phone, a smartphone, a tablet computer, a phablet, a general-purpose mobile computing device, a computer, a laptop. In an example embodiment, the communication apparatus 166 is a general-purpose off-the-shelf computing device, as opposed to a purpose-build proprietary equipment, whereby research & development costs will be lower as only the special-purpose software (and not the hardware) needs to be designed, implemented and tested. The communication apparatus 166 may employ a suitable operating system such as iOS, Android, or Windows Phone, for example. In an example embodiment, the user apparatus 166 runs a specific software application, which is used for controlling the apparatus 100.

In an example embodiment, the server apparatus 164 implements a user web service providing service to the user 168 (by receiving information from the apparatus 100, and providing information to the user apparatus 166, for example).

In an example embodiment, the server apparatus 164 may be implemented by a suitable computing resource or a combination of various computing resources. In an example embodiment, the computing resource 164 may be implemented as a single server computer or as a cluster of computers. The server is a part of the client-server computing model that acts as distributed application which partitions tasks or workloads between the provider of a resource or service, called server, and the service requester, called client. The server 164 may serve a number of apparatuses 100 and user apparatuses 166. The server computer 164 may be a host that is running one or more server programs which share their resources with clients 100, 166. The client 100, 166 may request a service function or content from the server 164. Also, the client 100, 166 may initiate a communication session with the server 164 which awaits incoming requests.

In an example embodiment, the server apparatus 164 may also operate according to the cloud computing model, at least in part. Naturally, besides these example embodiments of the server apparatus 164, other feasible computing architectures may be utilized as well to implement the hardware and software. Consequently, besides operating according to the client/server architecture, push technology may be utilized as well. In push technology, the request for a transaction is initiated by server apparatus 164, whereas with the pull technology the request for the information is initiated by the client 100, 166. In an example embodiment, the apparatus 100 is configured to be insertable into the natural material 150 so that the apparatus 100 further comprises a self-sufficient energy source 118 configured to provide electric energy for the apparatus 100, and a water-proof casing 116 encapsulating the apparatus 100.

In an example embodiment, the casing 116 is made of synthetic plastics. These include but are not restricted to Acrylonitrile butadiene styrene (ABS), Polyethylene terephthalate (PET), Polyurethane, Polycarbonate, Polyimide (PI), which are not prone to oxidation when in contact with damp material. The casing 100 is waterproof. The casing 116 may also be dust-proof and shock-proof. The casing 116 may be of any suitable shape. The casing 116 may be made of fluorescent or well visible material for recognition.

In an example embodiment, the self-sufficient, or independent, energy source 118 may be an electric battery converting stored chemical energy into electrical energy. The electric battery 118 may be rechargeable. In an example embodiment, the apparatus 100 may comprise a power interface to receive electrical energy for charging the battery 118. The power interface may couple the apparatus 100 to mains electricity, to a charger connector in a vehicle, or to some other power source enabling the charging of the battery 118. In addition to, or instead of, the battery 118, the apparatus 100 may comprise another portable energy source such as a solar cell converting the energy of light directly into electricity by the photovoltaic effect, or a fuel cell converting the chemical energy from a fuel into electricity through a chemical reaction with oxygen or another oxidizing agent.

In an example embodiment, the apparatus 100 may operate in a power saving mode to activate/de-activate the sensors during/after a measuring period.

In an example embodiment, each apparatus 100 is assigned a unique identifier, which may also be used in communication 134, 136 with the external entity 160. In this way, a plurality of apparatuses 100 is easier to manage by the external entity 160.

In an example embodiment, the apparatus 100 is a probe, which is inserted inside the natural material 150 at the time of collection or storage.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus for controlling fermentation of natural material, comprising:
   a water-proof casing configured to encapsulate the apparatus and make the apparatus a probe insertable into a bale made of the natural material;
   a self-sufficient energy source configured to provide electric energy for the apparatus;
   a container configured to contain a chemical reactive agent for limiting a fermentation process of the natural material of the bale;
   a valve coupled with the container;
   one or more sensors configured to measure at least one property of the natural material of the bale; and
   a controller, communicatively coupled with the one or more sensors and operatively coupled with the valve, configured such that the controller autonomously detects when the at least one property meets a predetermined threshold indicating that the fermentation process of the natural material of the bale has developed to a danger of spontaneous combustion of the natural material within the bale, and to control the valve to open so that the chemical reactive agent will be released into the natural material within the bale,
   wherein the container is positioned above the valve, whereby the opening of the valve causes the chemical reactive agent to flow into the natural material within the bale due to the Earth's gravity and/or the container is positioned above the valve, whereby the opening of the valve causes the chemical reactive agent to flow into the natural material within the bale due to the Earth's gravity, and/or the valve is coupled with a pump, whereby the opening of the valve causes the chemical reactive agent to flow into the natural material within the bale due to a pumping action by the pump.

2. The apparatus of claim 1, comprising:
   a radio transmitter, wherein the controller is configured to transmit data to an external entity, the data including one or more of the following: the measured at least one property, information about operation of the apparatus, and an alarm relating to an abnormal situation.

3. The apparatus of claim 1, wherein the at least one property is at least one of the following:
   a temperature of the natural material, a humidity of the natural material, and a pH of the natural material.

4. The apparatus of claim 1, wherein the natural material includes at least one of the following:
   an agricultural product, hay, straw, cereal, cotton, and peat.

5. The apparatus of claim 1, wherein the chemical reactive agent is selected to be at least one from a group which consists of:
   potassium carbonate, sodium carbonate, propionic acid, formic acid, acetic acid, sodium diacetate, anhydrous ammonia, sulphite, potassium sorbate.

6. The apparatus of claim 1, wherein the valve is coupled with a nozzle to control characteristics of a fluid flow of the chemical reactive agent.

* * * * *